(12) United States Patent
Zwislocki (10) Patent No.: US 8,107,638 B2
(45) Date of Patent: Jan. 31, 2012

(54) SEMI-INSERT HEARING PROTECTOR HAVING A HELMHOLTZ-TYPE RESONATOR

(75) Inventor: Jozef J. Zwislocki, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 232 days.

(21) Appl. No.: 12/049,444

(22) Filed: Mar. 17, 2008

(65) Prior Publication Data

US 2009/0232324 A1    Sep. 17, 2009

(51) Int. Cl.
*A61F 11/06* (2006.01)
(52) U.S. Cl. ............................ 381/72; 181/135; 128/864
(58) Field of Classification Search ................ 381/72, 381/71.6, 71.7, 73.1, 326, 328, 380, 382, 381/353, 345, 338; 128/864; 181/135, 130, 181/294, 207, 128, 126, 284, 175
See application file for complete search history.

(56) References Cited

U.S. PATENT DOCUMENTS

| | | | |
|---|---|---|---|
| 3,047,089 A * | 7/1962 | Zwislocki | 181/135 |
| 3,690,404 A | 9/1972 | Collins | |
| 3,909,776 A * | 9/1975 | Broding et al. | 181/119 |
| 4,571,746 A * | 2/1986 | Gorike | 2/209 |
| 5,824,967 A | 10/1998 | Zwislocki | |
| 5,983,399 A | 11/1999 | Falco et al. | |
| 6,095,146 A | 8/2000 | Knauer | |
| 6,678,897 B2 | 1/2004 | Lindgren | |
| 6,758,304 B1 | 7/2004 | McLean | |
| 7,740,104 B1 * | 6/2010 | Parkins et al. | 181/135 |
| 2006/0162992 A1 | 7/2006 | Seville | |

OTHER PUBLICATIONS

"Helmholtz Resonator—DiracDelta Science & Engineering Encyclopedia", http://diracdelta.co.uk/science/source/h/e/helmholtz%20resonator/source.html, Jan. 13, 2008, pp. 1-2.
"Helmholtz Resonator", http://physics.kenyon.edu/EarlyApparatus/Rudolf_Koenig_Apparatus/Helmholtz_Resonat..., Jan. 13, 2008, pp. 1-3.
"Helmholtz Resonance", http://www.phys.unsw.edu.au/jw/Helmholtz.html, Jan. 13, 2008, pp. 1-4.
"Acoustic/Flow-induced Oscillations of a Helmholtz Resonator", http://en.wikibooks.org/wiki/Acoustics/Flow-induced_oscillations_of_a_Helmholtz_reson..., Jan. 13, 2008, pp. 1-7.
"Helmholtz Resonant Absorber", http://www.audioholics.com/education/acoustics-principles/helmholtz-resonant-absorber, Jan. 13, 2008, pp. 1-2.
"Helmholtz Resonant Absorber—p. 2", http://www.audioholics.com/education/acoustics-principles/helmholtz-resonant-absorber/h..., Jan. 13, 2008, pp. 1-3.
International Search Report and Written Opinion for PCT/US2009/035045, mailed Oct. 21, 2009 (10 pages).

* cited by examiner

*Primary Examiner* — Vivian Chin
*Assistant Examiner* — Con P Tran
(74) *Attorney, Agent, or Firm* — Hiscock & Barclay, LLP (57) ABSTRACT

A semi-insert hearing protector includes a thin-walled enclosure sized substantially to that of the outer ear of a wearer, the enclosure being made from a rigid or semi-rigid material and secured to the head of said wearer by means of an adjustable headband. A short tube extends from the enclosure for communication with the ear canal, the short tube being made from a rigid or semi-rigid material and including a flexible cuff disposed over the tube made from a resilient material. The enclosure contains sound absorbing material configured to vary the frequency characteristic of sound attenuation by the semi-insert.

20 Claims, 5 Drawing Sheets

SEMI-INSERT HEARING PROTECTOR HAVING A HELMHOLTZ-TYPE RESONATOR

FIELD OF THE INVENTION

This invention relates to the field of hearing protection devices against excessive noise and in particular to a semi-insert hearing protector that employs a Helmholtz-type resonator.

BACKGROUND OF THE INVENTION

Growing recognition of hearing loss produced by excessive noise has increased the demand for hearing protectors and has accelerated improvements in their performance. Three types of hearing protectors have become known in the field; namely, i) earplugs that are inserted into the ear canal, ii) semi-inserts that seal the ear canal at its entrance, and iii) ear muffs that cover the entire outer ear. Each of the foregoing types of device has its own advantages and disadvantages. That is, earplugs are small and cheap on a unit basis and provide reasonable noise reduction when properly used. However, these devices pose hygiene problems due to the sensitivity of the ear canal to infection. Earplugs also tend to impact the ear canals with cerumen and become uncomfortable when worn over extended periods of time. These devices are also expensive in practical use because they have to be replaced often. Passive earmuffs can be very effective at high sound frequencies, but these devices provide inherently little noise reduction at low frequencies. Earmuffs are the most expensive and the most cumbersome of the devices in use. Introduction of an electro-acoustic feedback has improved their performance at low sound frequencies, but made the earmuffs more expensive and cumbersome. These devices also have the tendency to heat up the head, especially, in warm weather, creating additional discomfort for the wearer. Semi-inserts avoid the problems of earplugs because they do not enter the ear canal. They also are cheaper and much less cumbersome than earmuffs. Traditionally, however, these devices have provided the least noise reduction of the three noted types.

More recently, and as described in U.S. Pat. No. 5,824,967, Applicant has applied a new principle to semi-insert ear defenders. According to this principle and instead of closing the ear canal with a solid plug, a pair of tubes, referred to as "muffler tubes", are connected to the ear canal on each side of the head by means of a resilient cuff providing a tight seal around the ear canal. High noise reduction is achieved by making the acoustic impedance at the entrance of the tube much lower than the acoustic impedance at the entrance of the ear canal, such that acoustic energy flows into the tube rather than into the ear canal. The relatively low impedance can be produced in two cooperative ways—by making the tubes wider than the ear canals and by making their length equal to a quarter wave length of sound at medium audible frequencies. The bandwidth of the low impedance is increased by appropriate distribution of sound absorbing material in the tubes. The semi-inserts according to this design provide attributes making them desirable in that they are comfortable, less cumbersome than earmuffs, and can provide the highest noise reduction achieved thus far by any type of hearing protectors. These devices allow the noise reduction to be nearly evenly distributed over the audible frequency range, assuring optimum speech communication and music reception in noise.

In spite of the improvements that have been obtained by the new design, these semi-inserts have two known disadvantages. First, they may become cumbersome when helmets or hats are worn. Second, the long muffler tubes have been found not to be aesthetic by some wearers.

SUMMARY OF THE INVENTION

One object is to provide semi-insert hearing protectors that match or exceed the noise reduction achieved by the above described muffler-tube semi-inserts without having their disadvantages.

The foregoing object can be achieved by providing a semi-insert hearing protector with a Helmholtz-type resonator. A Helmholtz resonator generally consists of a short tube that opens into an enclosure having substantially larger linear dimensions. When the linear dimensions of the resonator are small compared to the incoming wavelength of sound, the tube acts as an acoustic inertance, while the enclosure acts as an acoustic compliance. This configuration is therefore an analog of an electric series network consisting of an inductance and a capacitance. The system then resonates at a frequency that can be described by the following mathematical equation:

$$f_r = (1/2\pi)(M/C)^{-1/2}$$

where $f_r$ is the resonance frequency, M, the tube inertance and C, the enclosure compliance. The inertance is defined as $$M = l\rho/S$$

in which l defines the length of the tube, $\rho$, is the density of air, and S defines the cross sectional area of the tube, wherein C is $$C = V/\rho c^2$$

with V being the volume of the enclosure, and c, the speed of sound.

The impedance of the resonator, as measured at the tube end is minimum at the resonance frequency. Its magnitude is determined there by the damping that is produced mainly by the friction of air motion in the tube and may be increased by placement of sound absorbing materials in the tube and/or the enclosure. The damping increases the bandwidth of the impedance minimum. By strategic distribution of the damping material in the enclosure, it is possible to shape the impedance distribution as a function of sound frequency.

The dimension of the outer ear can also allow the short tube to be designed so that the impedance at the entrance of the tube parallels the impedance at the entrance of the ear canal, but is substantially lower. As a result, high sound attenuation can be obtained at all sound frequencies below the resonance frequency of the ear, which is about 1000 Hz.

In the application to hearing protection, the tube of the resonator is connected to the ear canal via a resilient cuff that provides a tight seal around the entrance of the ear canal. For reasons of providing a tight seal, hygiene, and comfort the cross sections of the tube and of the sealing cuff are made sufficiently large to prevent the tube from entering the ear canal. The shape and the dimensions of the resonator and its damping, when needed, are so chosen as to provide an acoustic impedance at the tube entrance that is lower than the impedance at the entrance of the ear canal over a useful bandwidth of audible sound frequencies.

These and other features and advantages will be readily apparent from the following Detailed Description, which should be read in conjunction with the accompanying drawings.

DETAILED DESCRIPTION

The following description relates to certain preferred embodiments of a semi-insert hearing protector. It will be readily apparent to those of sufficient skill that variations and modifications are intended within the concepts described herein. In addition, certain terms are used throughout this description in order to provide a suitable frame of reference with regard to the accompanying drawings. These terms are not intended to be limiting, however, except where so specifically indicated.

Generally and according to the herein described design, a semi-insert hearing protector is provided comprising an enclosure that is compatible in size with the outer ear, but enclosing a volume of air of at least 7 cc, the enclosure being surrounded by thin walls made from a rigid or semi-rigid material. The enclosure is secured to the head of a wearer by means of a head band and designed for communication with the ear canal through a short tube having thin rigid or semi-rigid walls and a cuff made from a resilient material, the cuff and tube together forming an assembly having a combined cross section that exceeds the cross section of the ear canal at its entrance. Because ear canals vary in size and for reasons of hygiene and comfort, the cross section that is selected should be large enough to prevent the tube from entering even a large ear canal.

More specifically, a semi-insert hearing protector with a Helmholtz-type resonator is herein provided. This Helmholtz-type resonator generally consists of a short tube that opens into an enclosure having substantially larger linear dimensions. When the linear dimensions of the resonator are small compared to the incoming wavelength of sound, the tube acts as an acoustic inertance, while the enclosure acts as an acoustic compliance. This configuration is therefore an analog of an electric series network consisting of an inductance and a capacitance, employing a lumped parameter system. The system then resonates at a frequency that can be described by the following relationship:

$$f_r = (1/2\pi)(M/C)^{-1/2} \quad (1)$$

in which $f_r$ is the resonance frequency, M, the tube inertance and C, the enclosure compliance. The inertance (M) is defined as:

$$M = l\rho/S \quad (2)$$

in which l defines the length of the tube, $\rho$, is the density of air, and S defines the cross sectional area of the tube, wherein the compliance (C) is defined by:

$$C = V/\rho c^2 \quad (3)$$

with V being the volume of the enclosure, $\rho$, is the density of air, and c refers to the speed of sound.

The impedance of the resonator, as measured at the tube end, is minimum at the resonance frequency. Its magnitude is determined at the tube end by the damping that is produced mainly by the friction of air motion in the tube and may be increased by placement of sound absorbing materials in the tube and/or the enclosure. The damping increases the bandwidth of the impedance minimum. The dimension of the outer ear can also allow the short tube and the enclosure to be designed so that the impedance at the entrance of the tube parallels the impedance at the entrance of the ear canal as a function of sound frequency, but is substantially lower. As a result, high sound attenuation can be obtained at all sound frequencies below the resonant frequency of the ear, which is about 1000 Hz. By strategic distribution of the damping material in the enclosure, if required, it is therefore possible to shape the impedance distribution as a function of sound frequency.

In the application to hearing protection, the tube of the resonator is connected to the ear canal via a resilient cuff that provides a tight seal around the entrance of the ear canal. For reasons of providing a tight seal, hygiene, and comfort the cross section of the tube and sealing cuff, as assembled, is made sufficiently large to prevent the tube from entering the ear canal. The shape and the dimensions of the resonator and its damping are so chosen as to provide an acoustic impedance at the tube entrance that is lower than the impedance at the entrance of the ear canal over a useful bandwidth of audible sound frequencies.

Figure 1:
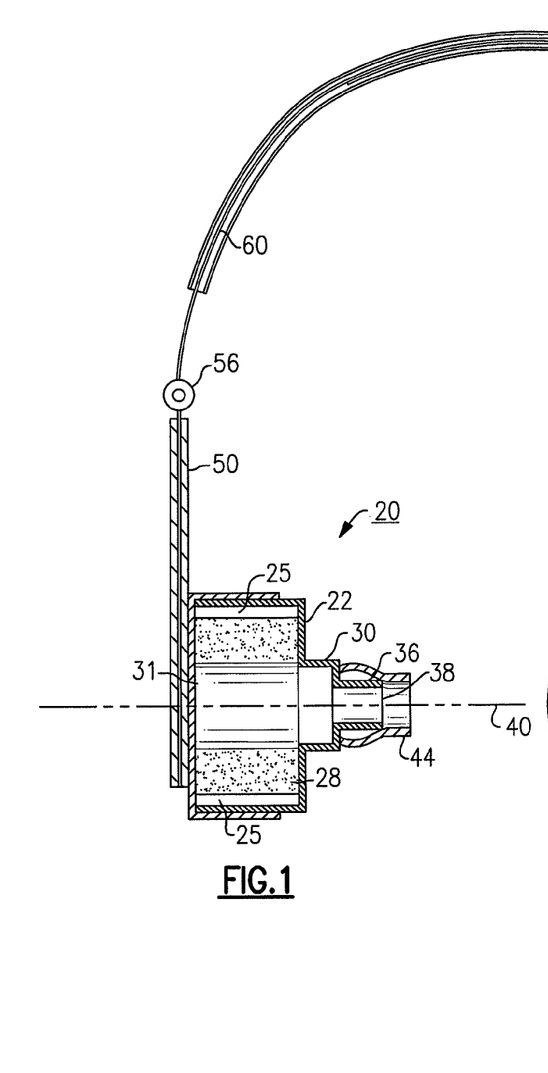
FIG. 1 is a partial side sectioned view of a hearing protector in accordance with a first embodiment.
Figure 2:
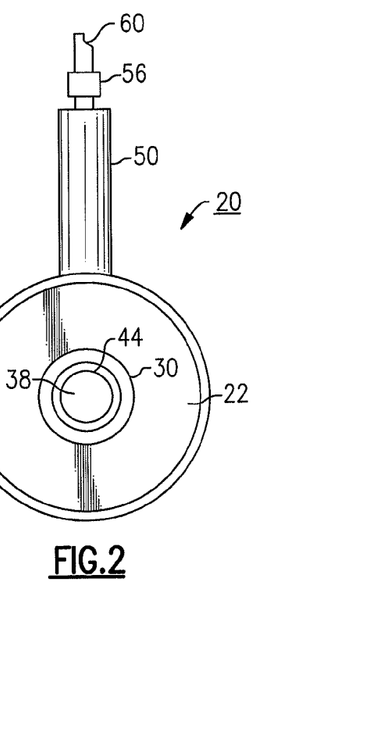
FIG. 2 is a partial end view of the hearing protector of FIG. 1.

With the preceding summary, certain preferred embodiments are shown and described according to FIGS. 1-11. Referring to FIGS. 1 and 2, a semi-insert hearing protector according to a first embodiment is shown, the hearing protector 20 consisting of a substantially cylindrical enclosure 22 consisting of thin walls of a rigid or semi-rigid material, such as polyvinylchloride (PVC). The enclosure 22 can be made as a unitary component or, according to this specific version, from multiple sections. The enclosure 22 is defined by an interior 25 having disposed therein a quantity of sound absorbing material 28, such as an open-cell foam rubber or plastic, the material being provided in an axial tubular-shaped configuration 31. The enclosure 22 further includes an elongated section 30 having a substantially circular, oval or elliptical cross section extending outwardly to a connecting tube 36, also having a circular, oval or elliptical cross section, the tube having an open distal end 38 extending from the interior 25 of the enclosure 22. The connecting tube 36 is designed for connection with the ear canal (not shown) wherein an exterior resilient cuff 44 is provided to enable a suitably tight seal for the hearing protector 20 at the entrance of the ear canal and in which the primary axis 40 of the connecting tube 36 extends through the open tubular configuration 31 of the contained sound-absorbing material 28 and is co-extensive therewith.

The enclosure 22 according to this embodiment is attached to a holder 50 by conventional means, the latter holding an adjustable headband 60 by means of a pivot connection 56. For purposes of the following discussion, the pivot connection is herein assumed to be provided between the holder 50 and the headband 60. Alternatively, the pivot could be provided integrally with the headband 60, wherein each configuration further enables convenient storage of the apparatus.

In operation, the tube of sound absorbing material 28 produces two effects. First through a damping effect, this tube 28 broadens the resonance curve of the Helmholtz resonance, thus broadening the frequency band of low impedance at medium audible sound frequencies (around 1000 Hz).

Second, the tubular configuration of sound absorbing material 28 further provides a substantial axial extension to the connecting tube 36 that is sufficient to produce a quarter-wave resonance in the broad vicinity of about 3000 Hz, which is higher than the resonance frequency of the ear (around 1000 Hz). Put another way, the sound frequency of the wave resonance is dependent on the effective length of the combined tube formed by the connecting tube 36 and the coaxial and coextensive tube of sound-absorbing material 28. The foregoing effect supplements the above-noted Helmholtz resonance at frequencies above 1000 Hz.

Figures 3, 4:
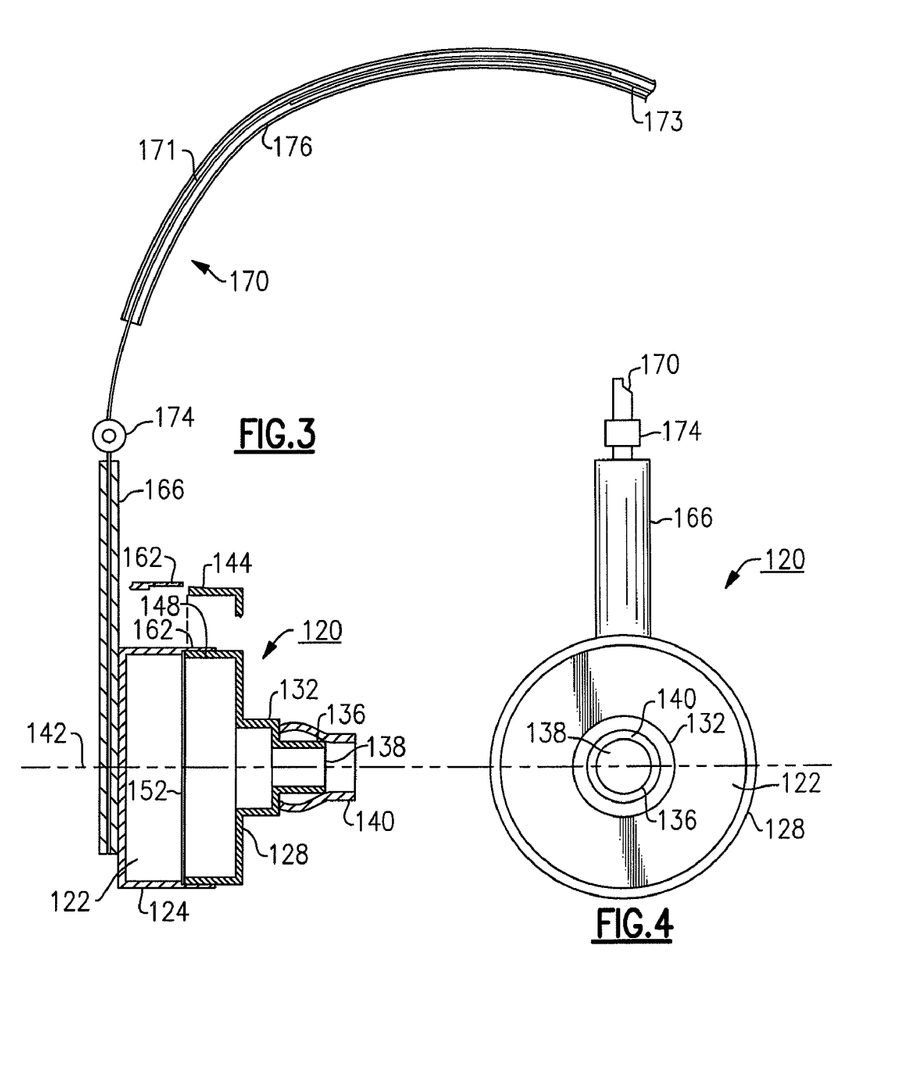
FIG. 3 is a partial side sectioned view of a hearing protector made in accordance with a second embodiment.
FIG. 4 is a partial end view of the hearing protector of FIG. 3.

Referring to FIGS. 3 and 4, there is shown a hearing protector 120 made in accordance with a second embodiment, this version serving as an alternative to that described in FIGS. 1 and 2. According to this design, the hearing protector 120 comprises two nearly equal, overlapping shells, 124 and 128, each of the shells being defined as thin-wall structures and made from a rigid or semi-rigid material that are tightly joined together, thereby defining an enclosure 122. Like the preceding design, one of the shells 128 includes an elongated portion 132 having a substantially circular, elliptical or oval cross section that extends outwardly to a tube 136, also having a circular, elliptical or oval cross section, the tube being designed for connection to the ear canal (not shown) through a resilient exterior cuff 140. According to this embodiment, a joint 144 formed between the two shells 124, 128 of the enclosure 122 is provided with a narrow annular shelf 148 that permits the placement of a porous, sound-absorbing plate 152 that is pressed into contact against the shelf by an edge 162 of the shell 124. This positioning is shown partially exploded according to FIG. 3.

The porous plate 152 can consist of one or several layers of diverse materials, some of which play a sound-absorbing role and some a supporting role. According to one version, the plate includes a supporting portion or layer as well as at least one sound-absorbing layer. Shell 124 is attached to a holder 166 that adjustably houses an adjustable headband 170, shown partially. The headband 170 consists of a pair of overlapping leaf springs 171, 173 that are housed within a tube 176. The length of an extending portion of the leaf springs 171, 173 from the tube 176 can be varied by the user to enable adjustment of the headband 170. A pivot 174 disposed between the headband 170 and the holder 166 allows the apparatus to be folded for easier storage in a pocket or similar holder (not shown). Only one of the hearing protectors 120 of the apparatus is shown for ease of explanation wherein the remaining hearing protector, including its connection to a holder and headband, is essentially a mirror image of the foregoing.

Figure 6:
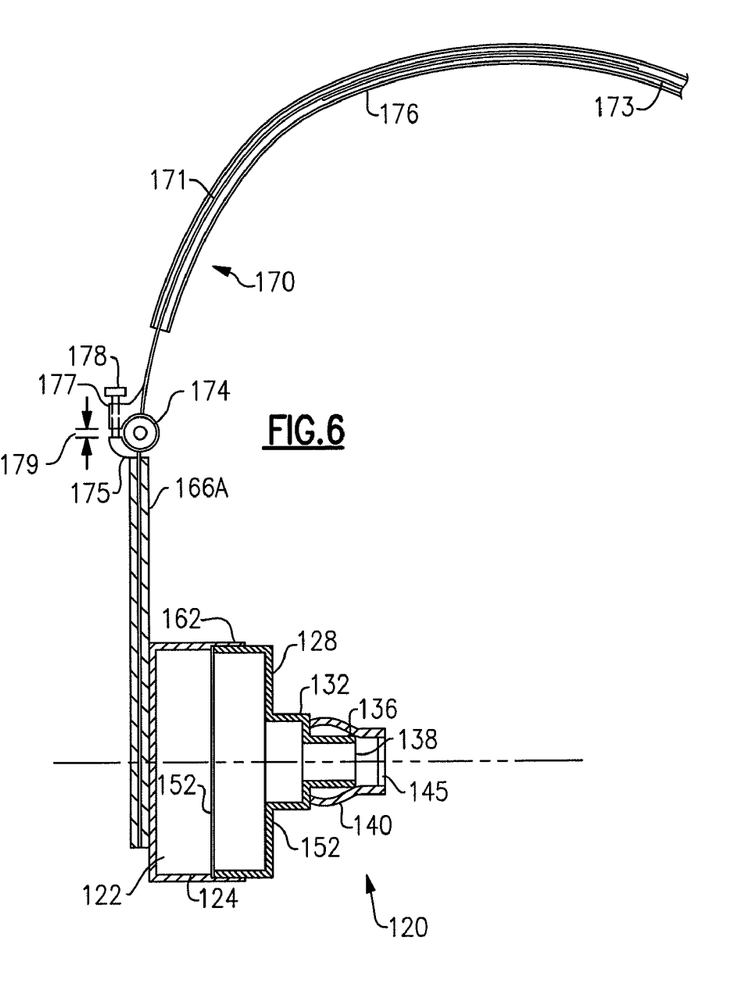
FIG. 6 is a partial side sectioned view of a hearing protector made in accordance with a third embodiment.

An alternative pivot design is shown in FIG. 6 for the hearing protector 120 in which a stop arrangement is provided about a pivot joint 174. Unlike the foregoing, adjustability is provided by means of a screw 178 in terms of a gap 179 provided within the holder 166A, the foregoing including shaped flanges 177, 179, respectively. Increasing the gap 179 by adjustment of the screw 178 has the effect of slightly changing the angle of the headband 170 and thereby increasing the pressure exerted on the ear by the flexible cuff 140. It has been determined that the foregoing pressure is essential in providing a proper and tight seal around the ear canal and assuring high noise insulation. Too much pressure, however, can create discomfort for the wearer. Due to individual differences in head sizes and the anatomical configuration around the ear canal, providing individual adjustment of the hearing protector 120 provides optimal settings.

Figure 7:
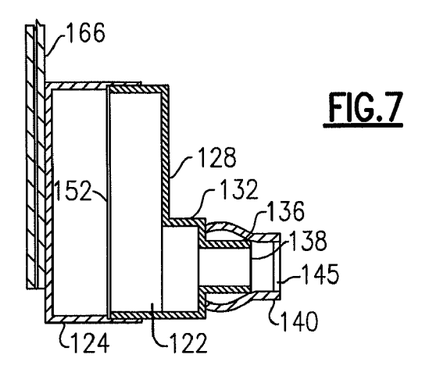
FIG. 7 is a partial side sectioned view of a modified version of the hearing protector of FIG. 6.

In addition, the flexible cuff can include a soft foam layer 145 at the distal tip, as shown in FIGS. 6 and 7. This layer 145 is made from a substantially softer material than the remainder of the cuff. The purpose of this added foam layer is to better conform to the ear part around the ear canal (not shown), without producing uncomfortable pressure.

In operation, the plate 152 of the herein described hearing protector 120 provides a negligible acoustic effect at low sound frequencies, such that the resonance frequency is determined by the interaction of the inertance of the tube 136 with the entire volume of air in the enclosure 122. As sound frequency is increased, however, the effect of the resistance of the plate 152 increases and gradually isolates the contents of shell 124 from the remainder of the enclosure 122. In this way, the effective acoustic compliance of the enclosure 122 is decreased (see equation (3)), and the resonance frequency according to the Helmholtz principle (see equation (1)) is increased. This results in broadening the frequency range of low impedance at the entrance of the tube 136.

An end view of the semi-insert hearing protectors 20, 120 according to FIGS. 2 and 4, respectively, illustrate concentric circular features in terms of the connecting tube and the enclosure. Moreover, each of the connecting tubes 36 and 136 are substantially centered along the profile of the enclosure of the hearing protector. It should be understood, however, that the shape or configuration of the enclosure can be replaced by an elliptical or oval configuration in order to enhance the aesthetic appearance of the semi-insert and satisfy specific requirements.

Figure 5:
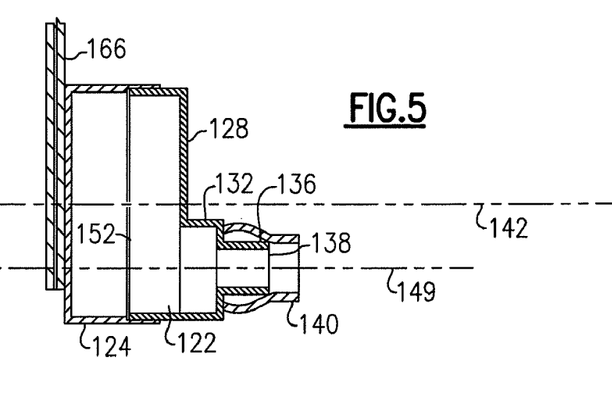
FIG. 5 is a partial side sectioned view of the hearing protector of FIGS. 3 and 4 in which the tube is eccentrically positioned.

Referring to FIG. 5, it should be further noted that the connecting tube 136 can be eccentrically positioned with regard to the enclosure 122 and more particularly in proximity with a longitudinal wall of the enclosure defined by the overlapping shells 124, 128. This positioning is further illustrated by a primary axis 149 of the tube 136, which is offset in relation to a primary axis 142 of the enclosure 122. Such positioning of the tube 136 may have acoustic advantages at high sound frequencies at which radial standing waves can arise in the enclosure 122 and produce a sound-pressure null in the center of the cylindrical enclosure. A similar configuration is depicted according to FIG. 7.

Figures 8, 9:
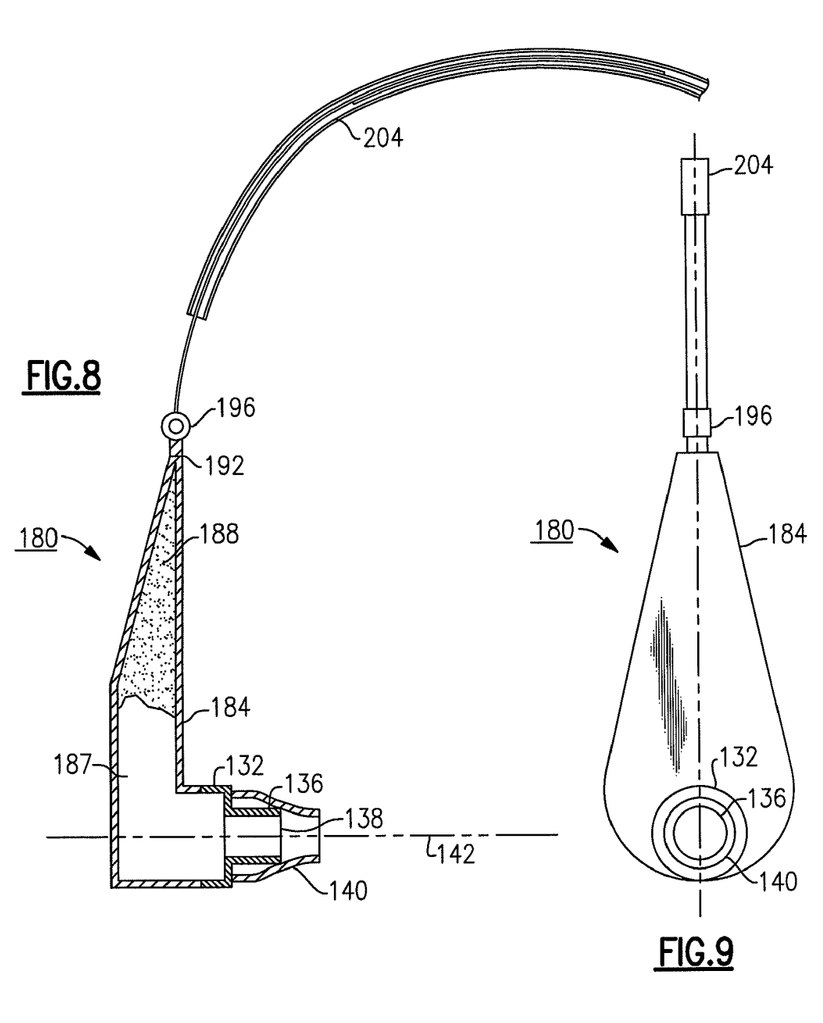
FIG. 8 is a partial side sectioned view of a hearing protector made in accordance with a fourth embodiment.
FIG. 9 is a partial end view of the hearing protector of FIG. 8.

Another embodiment of a semi-insert hearing protector in accordance with the invention is shown in FIGS. 8 and 9. According to this specific embodiment, the hearing protector 180 is defined by an enclosure 184 that has a substantially triangular, elongated shape extending to one narrow end 192 and which is hollow, being defined by an interior 187. A quantity of damping material 188, such as an open-cell rubber or plastic foam, is placed in the triangular narrow end 192 of the enclosure 184. The narrow end 192 is attached by means of a pivot 196, similar to those previously described, that is provided between a holder and an adjustable headband 204 that can be secured to the head (not shown) of a wearer. Otherwise, the enclosure 184 includes a unitary component or multiple components that are formed to include an elongated portion 132 having a connecting tube 136 further having an open end 138. The connecting tube 136 is designed for connection with the ear canal (not shown) wherein an exterior resilient cuff 140 is attached in overlaying relation, to enable a suitably tight seal for the hearing protector at the entrance of the ear canal and in which a primary axis 142 of the connecting tube 136 extends into the interior of the enclosure.

In terms of operation, the damping material 188 of this hearing protector provides a similar effect to that of the plate 152, FIG. 4, and the tube of sound absorbing material 28, FIG. 1, depending on the frequency of the entering sound. The configuration of FIGS. 8 and 9 and its variants illustrate additional aesthetic alternatives to the preceding designs and are illustrative of the flexibility in design that allows desired manipulation of noise-reduction characteristics. For example, the enclosure can be defined by a substantially globular shape as opposed to a cylindrical configuration. This latter shape would bring it the closest to the shape of a classical Helmholtz resonator.

Figure 10:
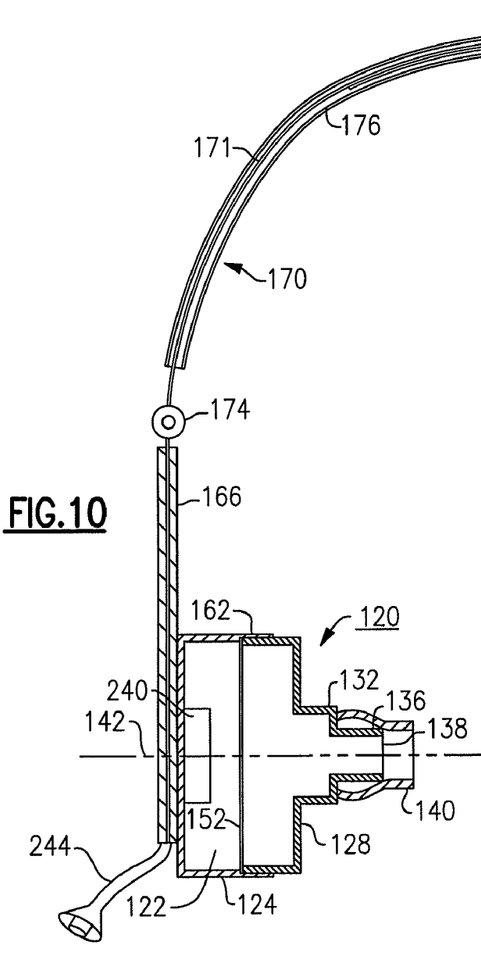
FIG. 10 is a partial side sectioned view of a hearing protector made in accordance with a fifth embodiment.
Figure 11:
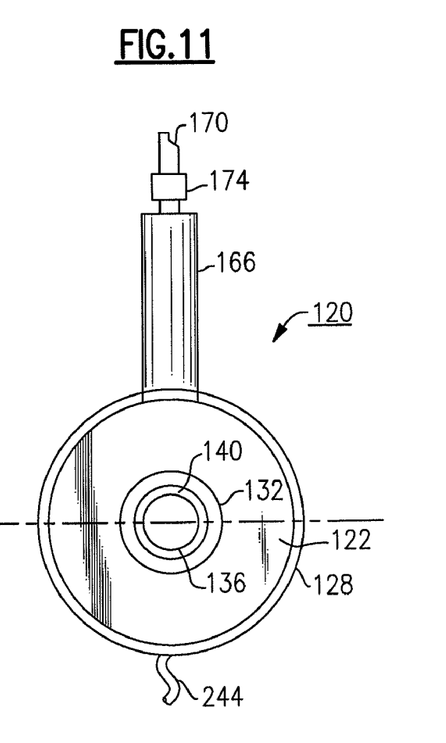
FIG. 11 is a partial end view of the hearing protector of FIG. 10.

In addition to the preceding, the herein described Helmholtz semi-insert can also be used for audio-communication. FIGS. 10 and 11 depict a semi-insert hearing protector that is similar to that previously described in FIGS. 3 and 4 but in which certain modifications have been made. Similar parts therefore include the same reference numerals for the sake of clarity. That is and for the above-stated purpose of audio communication, a small sound-emitting transducer can be suitably positioned within a top portion of the enclosure 122, as shown by number 240 in FIG. 10. In addition, a small microphone 244 can also be attached to the semi-insert assembly.

PARTS LIST FOR FIGS. 1-11

20 hearing protector
22 enclosure
25 interior
28 ring of sound-absorbing material
30 elongated section
31 tube, formed
36 tube
38 open end
40 primary axis
44 resilient cuff
50 holder
56 pivot
60 adjustable head band
120 semi-insert hearing protector
122 enclosure
124 shell
128 shell
132 enlarged portion
136 tube
138 open end, tube
140 exterior resilient cuff
142 primary axis—enclosure
144 joint
145 soft foam layer
148 shelf
149 axis—hearing protector
152 plate
162 edge
166 holder
166A holder
170 adjustable headband
171 leaf spring
173 leaf spring
174 pivot
175 flange
176 tube
177 flange
178 screw
179 gap
180 hearing protector
184 enclosure
187 interior, enclosure
188 damping material
192 narrow end
196 pivot
204 headband
208 tube
240 transducer
244 microphone While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

The invention claimed is:

1. A semi-insert hearing protector, said hearing protector comprising:
    an enclosure having an interior air volume of at least 7 cc and defining an initial acoustic compliance, said enclosure being defined by thin walls made from a rigid or semi-rigid material, said enclosure being secured to the head of a wearer by means of an adjustable headband;
    a short connecting tube extending from said enclosure for communication with the ear canal, said connecting tube being substantially narrower than said enclosure and being made from a rigid or semi-rigid material, said protector including a cuff disposed over said connecting tube, said cuff being made from a resilient material and having a cross section larger than the ear canal of a wearer to prevent said connecting tube from entering the ear canal, wherein said enclosure is entirely external relative to the ear of a wearer, said hearing protector having an acoustic impedance at a distal end of said connecting tube that is substantially smaller than the acoustic impedance at the entrance of the ear canal over a useful range of audible sound frequencies and in which said enclosure and said connecting tube interact with each other to form a Helmholtz-type resonator; and
    damping means for decreasing the initial acoustic compliance of said enclosure as sound frequency is increased, thereby increasing the bandwidth of the low acoustic impedance of said protector.

2. A hearing protector as recited in claim 1, in which the enclosure has a substantially cylindrical shape with at least one of a circular, oval and elliptical cross section and is further defined by a longitudinal wall.

3. A hearing protector as recited in claim 2, wherein said connecting tube and said cylindrical enclosure are each defined by a longitudinal axis, and in which said longitudinal axes are coextensive with one another such that said enclosure forms an extension of said connecting tube extending to said ear.

4. A hearing protector as recited in claim 2, wherein said connecting tube is placed eccentrically relative to said enclosure and is placed in relation to said longitudinal wall of said cylindrical enclosure.

5. A hearing protector as recited in claim 1, wherein said enclosure is defined by an asymmetrical oblong shape having a narrow end and a wide end, wherein said connecting tube is attached to the wide end of said enclosure.

6. A hearing protector as recited in claim 5, wherein said damping means includes sound-absorbing material disposed within said enclosure for the purpose of shaping the frequency characteristic of sound-attenuation and in which the sound-absorbing material is placed predominantly in the narrow end of said enclosure.

7. A hearing protector as recited in claim 1, wherein the enclosure is defined by a substantially globular shape.

8. A hearing protector as recited in claim 1, wherein said damping means includes sound absorbing material for the purpose of shaping the frequency characteristic of sound-attenuation.

9. A hearing protector as recited in claim 1, wherein said damping means includes sound-absorbing material contained in said enclosure for the purpose of shaping the frequency characteristic of sound-attenuation, said sound-absorbing material being configured in the shape of a tube having a longitudinal axis that is concentric with a longitudinal axis of said connecting tube and coextensive therewith.

10. A hearing protector as recited in claim 1, wherein said damping means includes sound-absorbing material contained in said enclosure for the purpose of shaping the frequency characteristic of sound-attenuation, said sound-absorbing material being configured as a stiff porous plate, said plate being arranged to divide said enclosure in two parts, one of said parts being connected to said connecting tube.

11. A hearing protector as recited in claim 1, wherein said resilient cuff includes a tip portion made from a material that is softer than the remaining material of said cuff.

12. A hearing protector as recited in claim 1, wherein said adjustable headband includes at least one pivot allowing said headband to be folded for convenient storage.

13. A hearing protector as recited in claim 12, wherein said pivot comprises a stop arrangement having means for limiting the maximum opening of said headband.

14. A hearing protector as recited in claim 1, wherein said resonator is configured to operate over the mid range of audible frequencies.

15. A hearing protector as recited in claim 1, wherein said enclosure further includes at least one electro-acoustic transducer.

16. A hearing protector as recited in claim 1, wherein said connecting tube and said enclosure interact to resonate at a frequency described by:

$$f_r = (1/2\pi)(M/C)^{-1/2}$$

in which $f_r$ equals the resonance frequency, M equals the acoustic inertance of the connecting tube of said hearing protector and C equals the acoustic compliance of the enclosure of said hearing protector.

17. A hearing protector as recited by claim 16, wherein the connecting tube inertance is defined by the relation $M=l\rho/S$, wherein l represents the effective length of said connecting tube, $\rho$ represents the density of air, and S represents the cross sectional area of the connecting tube and the acoustic compliance of said enclosure is defined by the relation $C=V/\rho c^2$, wherein V is the volume of said enclosure and c represents the speed of sound.

18. A hearing protector as recited in claim 1, wherein said connecting tube and said enclosure are each defined by a center axis, wherein the center axis of said connecting tube is coaxial with the center axis of said enclosure, thereby defining a single primary axis of said resonator.

19. A hearing protector as recited in claim 18, wherein the center axis of said connecting tube is linearly offset and parallel in relation to the center axis of said enclosure.

20. A method for manufacturing a semi-insert hearing protector, said method comprising the steps of:
   providing a connecting tube configured for communication with an ear canal of a subject, said connecting tube being made from one of a rigid or semi-rigid material;
   disposing a cuff over said connecting tube, said cuff being made from a resilient material and having a cross section larger than an ear canal of a wearer to create an effective seal with a subject while preventing said connecting tube and cuff from entering the ear canal, said enclosure being disposed entirely external to the ear of a wearer;
   providing an enclosure having an interior air volume of at least 7 cc and having an initial acoustic compliance, said enclosure having thin walls made from one of a rigid or semi-rigid material wherein said enclosure extends from a proximal end of said connecting tube and in which each of said enclosure and said connecting tube interact to form a Helmholtz-type resonator, said enclosure and said connecting tube being configured such that an acoustic impedance at a distal end of said connecting tube is substantially smaller than the acoustic impedance at the entrance of the ear canal over a useful range of audible sound frequencies, said enclosure further being provided with damping means for decreasing the initial acoustic compliance of said enclosure as sound frequency is increased, thereby increasing the bandwidth of the low acoustic impedance of said protector.

\* \* \* \* \*